United States Patent
Wang et al.

(10) Patent No.: US 9,517,019 B2
(45) Date of Patent: Dec. 13, 2016

(54) PHYSIOLOGY MEASUREMENT DEVICE AND SYSTEM, AND OPERATING METHOD OF WIRELESS SINGLE CHIP

(71) Applicant: PIXART IMAGING INC., Hsin-Chu County (TW)

(72) Inventors: Robert Cheng-Yuan Wang, Santa Clara, CA (US); Hsin-Chia Chen, Hsin-Chu County (TW)

(73) Assignee: PIXART IMAGING INC., Hsin-Chu County (TW)

( * ) Notice: Subject to any disclaimer, the term of this patent is extended or adjusted under 35 U.S.C. 154(b) by 0 days.

(21) Appl. No.: 15/144,535

(22) Filed: May 2, 2016

(65) Prior Publication Data

US 2016/0242657 A1    Aug. 25, 2016

Related U.S. Application Data

(63) Continuation-in-part of application No. 13/684,864, filed on Nov. 26, 2012, now Pat. No. 9,354,717.

(30) Foreign Application Priority Data

Feb. 20, 2012    (TW) .............................. 101105473 A

(51) Int. Cl.
```
A61B 5/026      (2006.01)
H04N 5/235      (2006.01)
A61B 5/00       (2006.01)
```
(52) U.S. Cl.
CPC ........... *A61B 5/0261* (2013.01); *A61B 5/0013* (2013.01); *A61B 5/441* (2013.01); *A61B 5/6843* (2013.01); *A61B 5/742* (2013.01); *H04N 5/2353* (2013.01); *H04N 5/2354* (2013.01); *A61B 2576/00* (2013.01)

(58) Field of Classification Search
CPC ... A61B 5/0066; A61B 5/0044; A61B 5/6824; G02B 27/48
See application file for complete search history.

(56) References Cited

U.S. PATENT DOCUMENTS

| | | | |
|---|---|---|---|
| 8,531,436 | B2 | 9/2013 | Lai et al. |
| 2005/0162375 | A1 | 7/2005 | Koay et al. |
| 2006/0033015 | A1 | 2/2006 | Feldmeier et al. |
| 2006/0203101 | A1 | 9/2006 | Silsby |

(Continued)

FOREIGN PATENT DOCUMENTS

| | | |
|---|---|---|
| CN | 101073047 A | 11/2007 |
| TW | 200606395 A | 2/2006 |
| TW | 201202652 A1 | 1/2012 |

*Primary Examiner* — Michael Teitelbaum
(74) *Attorney, Agent, or Firm* — Hauptman Ham, LLP

(57) ABSTRACT

There is provided a physiological measurement device including a light source, an image sensor and a processor. The light source illuminates a skin surface with a first brightness value and a second brightness value. The image sensor receives scattered light from tissues below the skin surface, and outputs a first image frame corresponding to the first brightness value and a second image frame corresponding to the second brightness value. The processor calculates an intensity comparison index between the first image frame and the second image frame, calculates perfusion data according to the first image frame and/or the second image frame, and identifies a contact status according to the intensity comparison index.

20 Claims, 9 Drawing Sheets

(56) References Cited

U.S. PATENT DOCUMENTS

| | | | |
|---|---|---|---|
| 2008/0234586 A1* | 9/2008 | Tearney | A61B 5/0059 600/479 |
| 2010/0103107 A1* | 4/2010 | Chao | G06F 3/0317 345/166 |
| 2011/0013002 A1* | 1/2011 | Thompson | A61B 5/0059 348/77 |

* cited by examiner

PHYSIOLOGY MEASUREMENT DEVICE AND SYSTEM, AND OPERATING METHOD OF WIRELESS SINGLE CHIP

CROSS REFERENCE TO RELATED APPLICATION

This application is a continuation-in-part application of U.S. application Ser. No. 13/684,864, filed Nov. 26, 2012, and claims the priority benefit of Taiwan Patent Application Serial Number 101105473, filed on Feb. 20, 2012, the full disclosures of which are incorporated herein by reference.

BACKGROUND

1. Field of the Disclosure

This disclosure generally relates to physiology measurement means and, more particularly, to physiology measurement means for measuring tissue perfusion and blood flow as well as capable of identifying a contact status with respect to a skin surface.

2. Description of the Related Art

The conventional optical mouse generally includes a light source, an image sensor and a processing unit, and is configured to be operated on a work surface by a user. The light source is configured to illuminate the work surface. The image sensor receives reflected light from the work surface to output image frames. The processing unit is configured to calculate a displacement of the optical mouse with respect to the work surface according to the image frames outputted from the image sensor, e.g. according to the correlation between the image frames.

In the above conventional optical mouse, when the processing unit identifies that an image quality of the image frames captured by the image sensor is poor, the displacement is not outputted so as to avoid cursor jitter or operating error. For example, when the optical mouse is lifted from the work surface by the user, the image quality is degraded. However, the image quality is generally degraded by the interference from noise or ambient light such that the processing unit may not be able to correctly output desired trace of the mouse and furthermore may not be able to enter a sleep mode. In other words, an expected accuracy cannot be achieved by determining whether to stop outputting the displacement only according to the image quality.

In addition, in an optical physiology measurement device, a contact status of the optical physiology measurement device with respect to a skin surface can significantly affect operation accuracy.

According, the present disclosure further provides an optical physiology measurement device that can effectively eliminate the interference from noise to improve the operation accuracy of the optical physiology measurement device.

SUMMARY

It is an object of the present disclosure to provide an optical physiology measurement device and system, and an operating method of a wireless single chip that may accurately identify whether a detection surface is stably attached a skin surface so as to improve the operation accuracy.

It is another object of the present disclosure to provide an optical physiology measurement device and an operating method of a wireless single chip that may wirelessly transmit calculated perfusion data and/or blood flow data to an external electronic device for being shown on a display screen.

It is another object of the present disclosure to provide an optical physiology measurement device and system that have a protection circuit configured as a laser hazard protector.

The present disclosure provides an optical physiology measurement device including a coherent light source, an image sensor and a processor. The coherent light source is configured to illuminate a skin surface in a first brightness value and a second brightness value different from the first brightness value. The image sensor is configured to receive scattered light from tissues under the skin surface, output a first image frame corresponding to the first brightness value and output a second image frame corresponding to the second brightness value. The processor is electrically coupled to the light source and the image sensor, and configured to calculate an intensity comparison index between the first image frame and the second image frame, identify a contact status of the image sensor with respect to the skin surface according to a comparison result of comparing the intensity comparison index with a threshold, and calculate tissue perfusion according to at least one of the first image frame and the second image frame.

The present disclosure further provides a physiology measurement system. The physiology measurement system includes an optical physiology measurement device and an electronic device. The optical physiology measurement device includes a coherent light source, an image sensor, a processor and a first communication interface. The coherent light source is configured to illuminate a skin surface in a first brightness value and a second brightness value different from the first brightness value. The image sensor is configured to receive scattered light from tissues under the skin surface, output a first image frame corresponding to the first brightness value and output a second image frame corresponding to the second brightness value. The processor is electrically coupled to the light source and the image sensor, and configured to calculate an intensity comparison index between the first image frame and the second image frame, identify a contact status of the image sensor with respect to the skin surface according to the intensity comparison index, and calculate tissue perfusion according to at least one of the first image frame and the second image frame. The first communication interface is configured to output the tissue perfusion. The electronic device is wirelessly coupled to the optical physiology measurement device and includes a second communication interface and a display device. The second communication interface is configured to receive the tissue perfusion from the optical physiology measurement device. The display device is configured to show the tissue perfusion on a screen thereof.

The present disclosure further provides an operating method of a wireless single chip. The wireless single chip includes a coherent light source, an image sensor and a processor. The operating method includes the steps of: controlling the coherent light source to illuminate a skin surface in a first brightness value and a second brightness value different from the first brightness value; acquiring, by the image sensor, a first image frame corresponding to the first brightness value and a second image frame corresponding to the second brightness value by receiving scattered light from tissues under the skin surface; calculate, by the processor, an intensity comparison index between the first image frame and the second image frame; identifying, by the processor, a contact status of the wireless single chip with respect to the skin surface according to a comparison result of comparing the intensity comparison index with a threshold; and calculating, by the processor, tissue perfusion according to at least one of the first image frame and the second image frame.

In an aspect, the processing unit further normalizes the average intensity difference (or the differential image) with an exposure parameter, wherein the exposure parameter may be at least one of a drive intensity of the light source, an exposure time and an image gain, so as to improve the identification accuracy.

In an aspect, the processing unit further identifies the operating state according to the average intensity difference associated with the illumination of the light source having different features and a threshold, wherein said different features may be emitting light of different wavelengths, or emitting coherent light and non-coherent light.

In an aspect, the processing unit may control (directly or through the light control unit) one light source to monotonically change its brightness value and identify whether the average intensity difference (or the average intensity) is changed corresponding to the brightness value so as to improve the identification accuracy by double-checking, wherein the operating state is identified as a lift state when the processing unit identifies that the average intensity difference is not changed corresponding to the changing of the brightness value.

In an aspect, the processing unit may further monotonically change an exposure parameter (e.g. an exposure time) of the image sensor and identify whether the average intensity difference (or the average intensity) is changed corresponding to the exposure parameter so as to improve the identification accuracy by double-checking, wherein the operating state is identified as a lift state when the processing unit identifies that the average intensity difference is not changed corresponding to the changing of the exposure time.

In the optical navigation device of the present disclosure, when the processing unit identifies that the average intensity difference is smaller than the at least one threshold, it indicates that the optical navigation device may be lifted by a user; therefore the processing unit controls the optical navigation device to enter a sleep mode to avoid possible mistakes. In addition, to further improve the identification accuracy, it is able to utilize a different light source, to monotonically change a brightness value of the light source or to monotonically change an exposure parameter to double check the operating state.

BRIEF DESCRIPTION OF THE DRAWINGS

Other objects, advantages, and novel features of the present disclosure will become more apparent from the following detailed description when taken in conjunction with the accompanying drawings.

DETAILED DESCRIPTION OF THE EMBODIMENT

It should be noted that, wherever possible, the same reference numbers will be used throughout the drawings to refer to the same or like parts.

Figure 1:
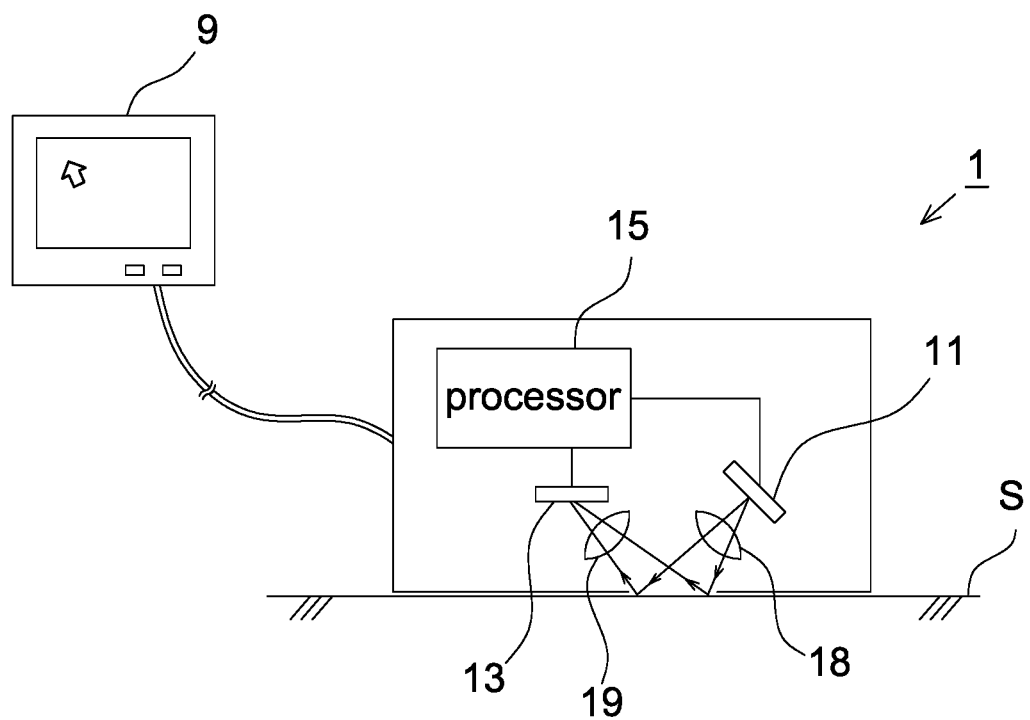
FIG. 1 is a schematic diagram of the optical navigation device according to an embodiment of the present disclosure.

Referring to FIG. 1, it shows a schematic diagram of the optical navigation device according to an embodiment of the present disclosure. The optical navigation device 1 is configured to be operated by a user on a work surface S for detecting a motion, e.g. a displacement or a speed, with respect to the work surface S. The motion is transmitted to an electronic device 9 having a display to control an application executed by the electronic device 9 or a movement of a cursor shown on the display.

The optical navigation device 1 includes at least one light source 11, an image sensor 13 and a processing unit 15. In other embodiments, the optical navigation device 1 may further include at least one optical component 18 configured to adjust an illumination area of the light source 11 and an optical component 19 configured to adjust the sensing efficiency of the image sensor 13, wherein structures of the optical components 18 and 19 do not have any limitation. The light source 11 may be a light emitting diode or a laser diode, and is configured to emit light of a predetermined center wavelength, preferably emitting infrared light or invisible light. The image sensor 13 may be a CCD image sensor, a CMOS image sensor or other sensors configured to detect images. The processing unit 15 may be a processor capable of processing image data without any limitation.

Figure 2:
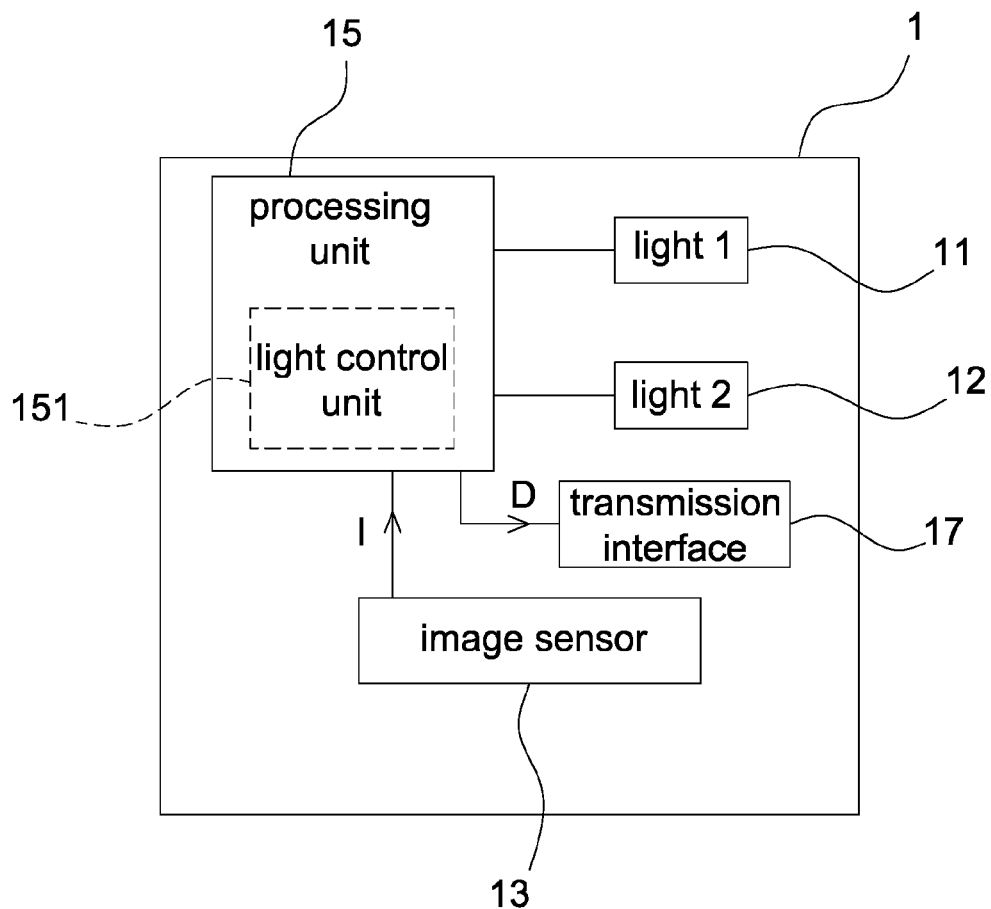
FIG. 2 is a schematic block diagram of the optical navigation device according to an embodiment of the present disclosure.

Referring FIGS. 1 and 2, FIG. 2 shows a schematic block diagram of the optical navigation device according to an embodiment of the present disclosure. The optical navigation device 1 includes a first light source 11, a second light source 12, the image sensor 13, the processing unit 15 and a transmission interface 17. In this embodiment, the optical navigation device 1 may include only one light source, e.g. the first light source 11, according to different applications.

The light sources 11 and 12 illuminate the work surface S in a first brightness value and a second brightness value, wherein the first brightness value is different from the second brightness value. For example, the first brightness value is larger than the second brightness value, and the second brightness value may be zero brightness or non-zero brightness. In this embodiment, the first light source 11 and the second light source 12 may have different illuminating features; for example, the first light source 11 and the second light source 12 may emit light of different wavelengths, or one of the first light source 11 and the second light source 12 is a coherent light source and the other one is a non-coherent light source.

The image sensor 13 receives reflected light from the work surface S and outputs a first image frame $I_1$ corresponding to the first brightness value and a second image frame $I_2$ corresponding to the second brightness value. Preferably, the image sensor 13 alternatively outputs the first image frame $I_1$ and the second image frame $I_2$ when operating continuously.

The processing unit 15 is configured to control the light sources 11 and 12 to illuminate the work surface S, to calculate a differential image of the first image frame $I_1$ and the second image frame $I_2$ temporally adjacent to each other, to calculate an average intensity of the differential image (i.e. an average intensity difference of the first image frame $I_1$ and the second image frame $I_2$), to calculate a displacement according to the differential image (e.g. according to the correlation between two differential images), and to identify an operating state according to the average intensity of the differential image (e.g. according to a comparison result of comparing the average intensity or the average intensity difference with at least one threshold), wherein the operating state may include a normal state in which the optical navigation device 1 is being operated on the work surface S and a lift state in which the optical navigation device 1 is being lifted by a user.

In one embodiment, the processing unit 15 identifies the comparison result of comparing the average intensity (or the average intensity difference) with at least one threshold so as to identify the operating state. For example, when the average intensity is larger than the threshold, the optical navigation device 1 is in a normal state; that is, the image sensor 13 can still receive enough reflected light from the work surface S. However, when the average intensity is smaller than the threshold, the optical navigation device 1 is in a lift state; that is, the image sensor 13 cannot receive enough reflected light. When the processing unit 15 identifies a lift state, the processing unit 15 controls the optical navigation device 1 to enter a sleep mode and stop outputting a displacement D. The displacement D is normally sent to the electronic device 9 wired or wirelessly through the transmission interface 17, wherein the transmission interface 17 may be wired or wireless interfaces well known to the art.

In another embodiment, the processing unit 15 further normalizes the average intensity (or the average intensity difference) with an exposure parameter so as to increase the identification accuracy, wherein the exposure parameter may be at least one of a drive intensity of the light source, an exposure time and an image gain. In one embodiment, the drive intensity of the light source may be a driving current or a driving voltage of the light source. The processing unit 15 identifies the operating state by identifying a comparison result of comparing a normalized average intensity (or a normalized average intensity difference) with at least one threshold. In this embodiment, the normalization may be implemented by dividing the average intensity (or the average intensity difference) by the exposure parameter.

In another embodiment, the optical navigation device 1 may further include a light control unit 151 configured to control the light source 11 and/or 12 to illuminate in the first brightness value and the second brightness value, wherein the light control unit 151 may be included in the processing unit 15 (as shown in FIG. 2) or separated from the processing unit 15 without any limitation. In other words, in this embodiment the processing unit 15 may controls the illumination of the light source 11 and/or 12 directly or through the light control unit 151.

Figure 3:
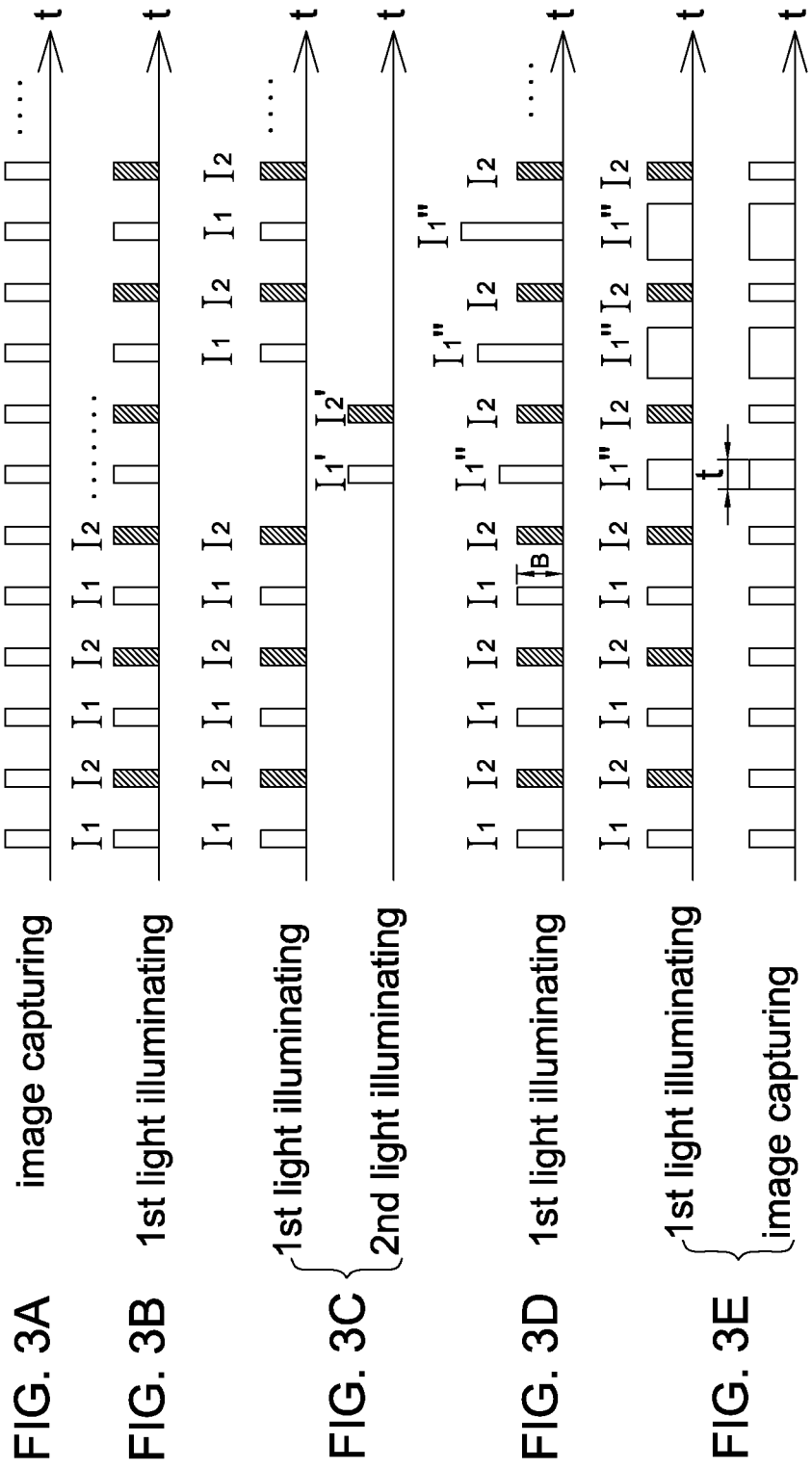
FIGS. 3A-3E are operational schematic diagrams of the optical navigation device according to the embodiment of the present disclosure.

Referring to FIGS. 3A-3E, they show operational schematic diagrams of the optical navigation device 1. FIG. 3A shows a schematic diagram of the image capturing of the image sensor 13, e.g. capturing image frames at a fixed sampling frequency; FIG. 3B shows a schematic diagram of the illumination of the first light source 11; FIG. 3C shows a schematic diagram of the illumination of the first light source 11 and the second light source 12 in another embodiment; FIG. 3D shows a schematic diagram of the illumination of the first light source 11 in another embodiment; and FIG. 3E shows a schematic diagram of the illumination of the first light source 11 and the image capturing of the image sensor 13 in another embodiment; wherein the illumination of the first light source 11 and the second light source 12 corresponds to the image capturing of the image sensor 13.

Figure 4:
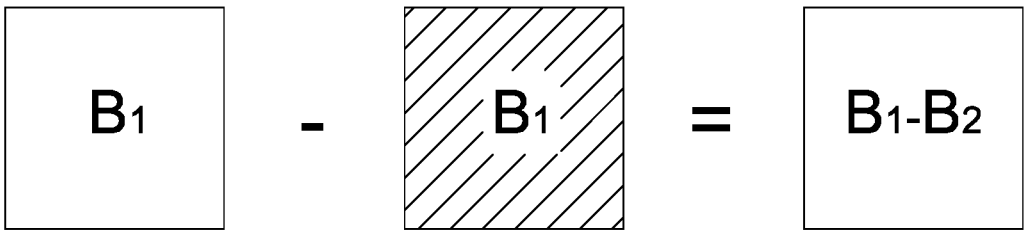
FIG. 4 is a schematic diagram of calculating a differential image by the optical navigation device according to the embodiment of the present disclosure.

Referring to FIGS. 3A, 3B and 4, in this embodiment the optical navigation device 1 includes only one light source (e.g. the first light source 11 or the second light source 12), and the first light source 11 is taken as an example herein. The processing unit 12 controls (directly or through the light control unit 151) the first light source 11 to illuminate the work surface S in a first brightness value and a second brightness value. The image sensor 13 receives reflected light from the work surface S and outputs first image frames $I_1$ corresponding to the first brightness value and second image frames $I_2$ corresponding to the second brightness value. The processing unit 15 calculates a differential image $(I_1-I_2)$ of the first image frames $I_1$ and the second image frames $I_2$ temporally adjacent to each other, calculates a displacement according to the differential image $(I_1-I_2)$, and identifies an operating state according to an average intensity $(B_1-B_2)$ of the differential image $(I_1-I_2)$, wherein the average intensity (or the average intensity difference) may be calculated by: (1) calculating a first intensity $B_1$ of the first image frame $I_1$ and a second intensity $B_2$ of the second image frame $I_2$ at first and then calculating a difference (or an average intensity difference) of the first intensity $B_1$ and the second intensity $B_2$; or (2) calculating the differential image (IA) at first and then directly calculating the average intensity $(B_1-B_2)$ of the differential image $(I_1-I_2)$. When the average intensity $(B_1-B_2)$ is smaller than a predetermined threshold, the operating state is identified as a lift state and the processing unit 15 controls the optical navigation device 1 to enter a sleep mode and/or stop outputting the displacement D.

In the above embodiments, as the interference from ambient light and noise have been eliminated by calculating the differential image, the identification accuracy is improved. Next, to further increase the identification accuracy, the present disclosure further provides various embodiments to confirm whether the optical navigation device 1 is lifted or not. Said confirmation may be performed in the following conditions: the average intensity (or the normalized average intensity) being smaller than the threshold, every predetermined time interval in normal state, or the average intensity (or the normalized average intensity) being smaller than a confirmation threshold, wherein the confirmation threshold may be larger than the predetermined threshold so as to distinguish an uncertain lift state. The merit of the following embodiments is to further increase the identification accuracy since different work surfaces may have different reflectance toward different light sources to degrade the intensity of reflected light thereby decreasing the average intensity and introducing error.

Referring to FIGS. 3A, 3C and 4, in this embodiment the optical navigation device 1 includes the first light source 11 and the second light source 12. In normal operation, the processing unit 15 controls (directly or through the light control unit 151) the first light source 11 to illuminate the work surface S in a first brightness value and a second brightness value. The image sensor 13 receives reflected light from the work surface S and outputs first image frames $I_1$ corresponding to the first brightness value and second image frames $I_2$ corresponding to the second brightness value. The processing unit 15 calculates a first differential image $(I_1-I_2)$ and a first average intensity $(B_1-B_2)$ of the first image frames $I_1$ and the second image frames $I_2$ and identifies whether the first average intensity (or the first intensity difference) is smaller than a first threshold. In the above confirmation conditions (e.g. the first average intensity being smaller than the first threshold), the processing unit 15 controls (directly or through the light control unit 151) the second light source 12 to illuminate the work surface S in a third brightness value and a fourth brightness value. The image sensor 13 receives reflected light from the work surface S and outputs first image frames corresponding to the third brightness value and second image frames $I_2'$ corresponding to the fourth brightness value. The processing unit 15 calculates a second differential image $(I_1'-I_2')$ and a second average intensity $(B_1-B_2)$ of the first image frames $I_1'$ and the second image frames $I_2'$ and identifies whether the second average intensity $(B_1-B_2)$ is smaller than a second threshold. When the second average intensity (or the second intensity difference) is smaller than the second threshold, the operating state is identified as a lift state and the processing unit 15 controls the optical navigation device 1 to enter a sleep mode and/or stop outputting the displacement D. When the second average intensity (or the second intensity difference) is still larger than the second threshold, the normal mode is maintained in which the operation may be held by using the first light source 11 or changing to use the second light source 12. It is appreciated that the processing unit 15 may control the first light source 11 and the second light source 12 in a reverse sequence. In other words, in this embodiment the processing unit 15 calculates a first average intensity difference corresponding to the illuminating of the first light source 11 and a second average intensity difference corresponding to the illuminating of the second light source 12, and identifies the operating state according to a comparison result of comparing the first average intensity difference with a first threshold and comparing the second average intensity difference with a second threshold; or the processing unit 15 calculates a first differential image corresponding to the illuminating of the first light source 11 and a second differential image corresponding to the illuminating of the second light source 12, and identifies the operating state according to an average intensity of the first differential image and the second differential image. In this embodiment, the first threshold may be identical to or different from the second threshold; the first brightness value may be identical to or different from the third brightness value; and the second brightness value may be identical to or different from the fourth brightness value.

Referring to FIGS. 3A, 3D and 4, in this embodiment the optical navigation device 1 includes only one light source (e.g. the first light source 11 or the second light source 12), and the first light source 11 is taken as an example herein. In normal operation, the processing unit 15 controls (directly or through the light control unit 151) the first light source 11 to illuminate the work surface S in a first brightness value and a second brightness value. The image sensor 13 receives reflected light from the work surface S and outputs first image frames $I_1$ corresponding to the first brightness value and second image frames $I_2$ corresponding to the second brightness value. The processing unit 15 calculates a differential image $(I_1-I_2)$ and an average intensity $(B_1-B_2)$ of the first image frames $I_1$ and the second image frames $I_2$ and identifies whether the average intensity $(B_1-B_2)$ is smaller than a first threshold. In the above confirmation conditions (e.g. the average intensity being smaller than the predetermined threshold), the processing unit 15 controls (directly or through the light control unit 151) the first light source 11 to monotonically change the first brightness value (e.g. herein the first brightness B is monotonically increased but it may be monotonically decreased in another embodiment). The image sensor 13 receives reflected light from the work surface S and outputs first image frames $I_1''$ corresponding to the changed first brightness value and second image frames $I_2$ corresponding to the second brightness value. The processing unit 15 calculates a differential image $(I_1''-I_2)$ and an average intensity $(B_1-B_2)$ of the first image frames $I_1''$ and the second image frames $I_2$ and identifies whether the average intensity $(B_1-B_2)$ is changed corresponding to the first brightness value B. If the average intensity $(B_1-B_2)$ is not changed corresponding to the changing of the first brightness value B, the operating state is identified as a lift state and the processing unit 15 controls the optical navigation device 1 to enter a sleep mode and/or stop outputting the displacement D. In another embodiment, the processing unit 15 may further monotonically change the second brightness value of the light source (e.g. the first brightness value being smaller than the second brightness value), and identifies whether the average intensity of the differential image is changed corresponding to the changing of the second brightness value.

Referring to FIGS. 3E and 4, in this embodiment the optical navigation device 1 includes only one light source (e.g. the first light source 11 or the second light source 12), and the first light source 11 is taken as an example herein. In normal operation, the processing unit 15 controls (directly or through the light control unit 151) the first light source 11 to illuminate the work surface S in a first brightness value and a second brightness value. The image sensor 13 receives reflected light from the work surface S and outputs first image frames $I_1$ corresponding to the first brightness value and second image frames $I_2$ corresponding to the second brightness value. The processing unit 15 calculates a differential image $(I_1-I_2)$ and an average intensity $(B_1-B_2)$ of the first image frames $I_1$ and the second image frames $I_2$ and identifies whether the average intensity $(B_1-B_2)$ is smaller than a first threshold. In the above confirmation conditions (e.g. the average intensity being smaller than the predetermined threshold), the processing unit 15 controls the image sensor 13 to monotonically change an exposure parameter thereof (e.g. herein an exposure time t is monotonically increased but it may be monotonically decreased in another embodiment). Meanwhile an interval of the first light source 11 illuminating in the first brightness value is preferably controlled to change corresponding to or keeping longer than the exposure time t. The image sensor 13 receives reflected light from the work surface S and outputs first image frames $I_1''$ corresponding to the first brightness value and second image frames $I_2$ corresponding to the second brightness value. The processing unit 15 calculates a differential image $(I_1''-I_2)$ and an average intensity $(B_1-B_2)$ of the first image frames $I_1''$ and the second image frames $I_2$ and identifies whether the average intensity $(B_1-B_2)$ is changed corresponding to the changing of the exposure parameter. If the average intensity ($B_1$–$B_2$) is not changed corresponding to the changing of the exposure parameter, the operating state is identified as a lift state and the processing unit 15 controls the optical navigation device 1 to enter a sleep mode and/or stop outputting the displacement D.

In the above embodiments, for example monotonically increased current may be used to drive the light source and if the average intensity is increased correspondingly, it is able to confirm that the optical navigation device is not lifted. Therefore, no matter whether the average intensity is smaller than the threshold, the optical navigation device may keep working and will not enter the sleep mode. In the above embodiments, it is able to fix the light intensity but monotonically increase the exposure parameter, and if the average intensity is increased correspondingly, it is able to confirm that the optical navigation device is not lifted. Therefore, no matter whether the average intensity is smaller than the threshold, the optical navigation device may keep working and will not enter the sleep mode. The above methods may be applied to the optical navigation device including a single light source or a plurality of light sources.

The above method of identifying a lift state is also applicable to an optical physiology measurement means. In the optical physiology measurement means, a contact status of the optical physiology measurement means with respect to a skin surface under detection is vital for obtaining accurate data.

Since an optical physiology measurement device of the present disclosure is applicable to a wearable electronic device or a portable electronic device, a detection surface of the optical physiology measurement device can have a movement relative to or is not stably attached to a skin surface under detection due to the motion of a user, the measured data can be significant affected by the unstable measuring condition. In this embodiment, when it is identified that the detection surface of the optical physiology measurement device is not stably or tightly attached to the skin surface (e.g., an intensity comparison index smaller or larger than a threshold, described later), the optical physiology measurement device stops outputting the calculated tissue perfusion or blood flow.

Figure 5:
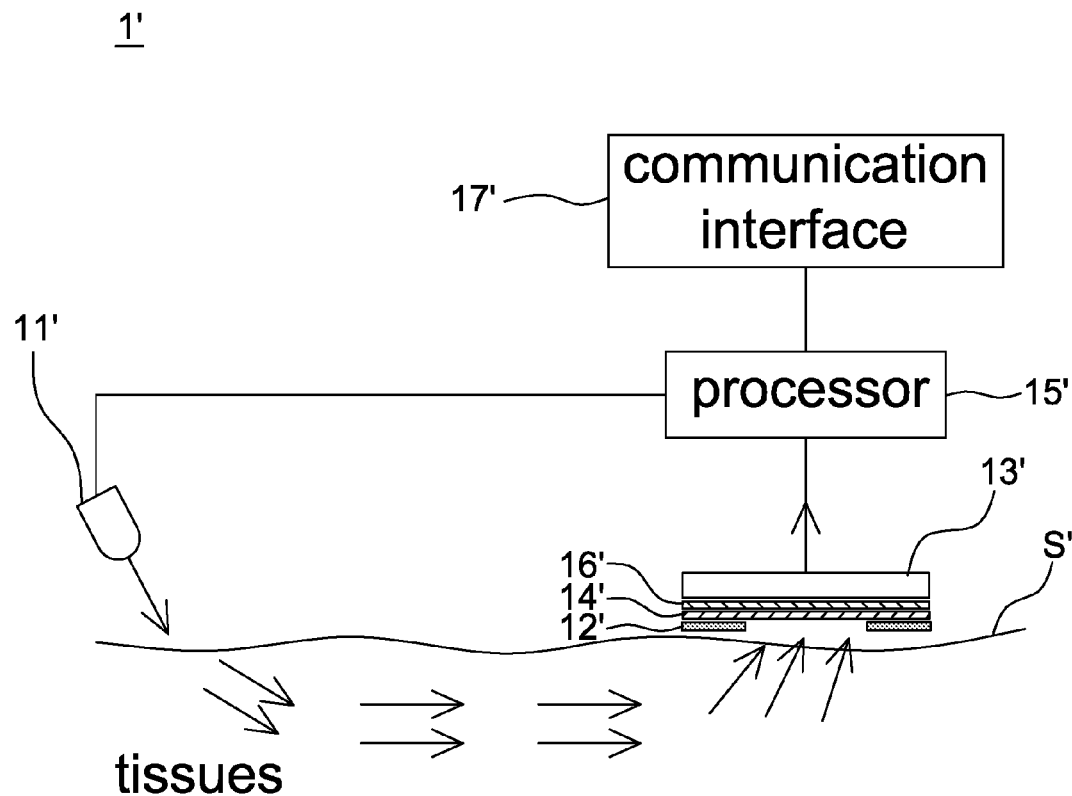
FIG. 5 is a schematic diagram of an optical physiology measurement device according to an alternative embodiment of the present disclosure.
Figures 6A, 6B:
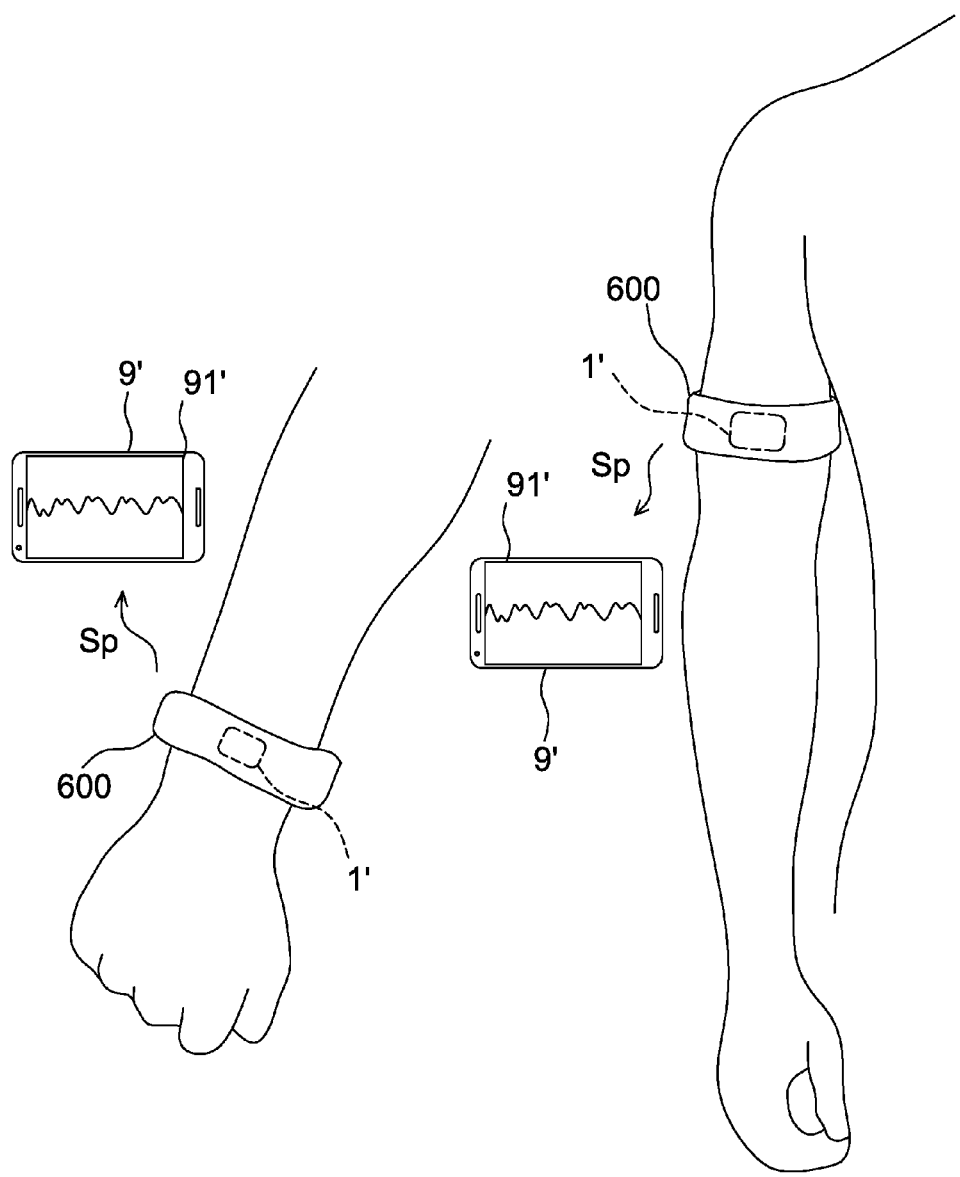
FIGS. 6A-6B are operational schematic diagrams of an optical physiology measurement system according to an alternative embodiment of the present disclosure.

Referring to FIG. 5, it is a schematic diagram of an optical physiology measurement device 1' according to one embodiment of the present disclosure. Preferably, the optical physiology measurement device 1' is encapsulated as a wireless single chip such that the optical physiology measurement device 1' is easily integrated in a wearable device 600 as shown in FIGS. 6A and 6B. The wireless single chip (i.e. the optical physiology measurement device 1') is configured to output the measured tissue perfusion and/or blood flow to an external electronic device 9' having a display screen.

FIGS. 6A and 6B are operational schematic diagrams of an optical physiology measurement system, which includes the wearable device 600 with the optical physiology measurement device 1' integrated therein and an electronic device 9' having a display device 91'. It should be mentioned that although FIG. 6A shows that the wearable device 600 is a wristlet and FIG. 6B shows that the wearable device 600 is an armband, they are only intended to illustrate but not to limit the present disclosure. In other embodiments, the wearable device 600 is any suitable accessory or ornament such as a finger ring, foot ring, necklace, watch, glasses or others having a contact with at least a part of skin of a human body when it is worn on the human body. In other embodiments, the optical physiology measurement device 1' is integrated in a portable electronic device, fixed equipment or home appliance without particular limitations.

Although FIGS. 6A and 6B show that the electronic device 9' is a portable electronic device such as a mobile phone, a personal digital assistant, a tablet computer, it is only intended to illustrate but not to limit the present disclosure. In other embodiments, the electronic device 9' is a fixed equipment as long as it has a display device 91' for showing the tissue perfusion and/or blood flow measured by the optical physiology measurement device 1'.

More specifically, in the present disclosure, the optical physiology measurement device 1' has the measurement function but does not have the displaying function such that is has a small size and weight to be worn comfortably by a user; whereas, the electronic device 9' has the displaying function but does not have the measurement function. The electronic device 9' is any suitable movable or unmovable device. In some applications, the electronic device 9' further has the function of long-term recording the tissue perfusion and/or blood flow, which can be served as a reference for the health monitoring of a user. In some applications, the electronic device 9' further has the warning function when the monitored or recorded physiological data appears unusual conditions, and automatically communicates with the related agency or person through, for example, internet or wireless phone system, but not limited thereto. In other applications, the measurement function of the optical physiology measurement device 1' and the displaying function of the electronic device 9' are coupled by an application (APP) such that any authorized user can easily observe the measured results as long as the application is run (e.g., clicking an icon shown on a display screen of the electronic device 9').

Figure 8:
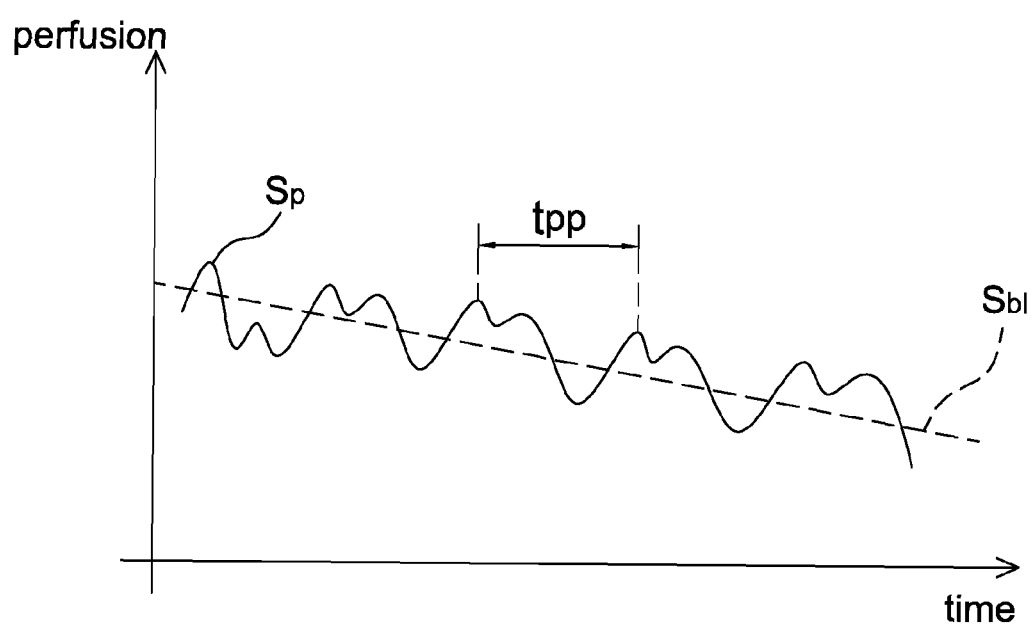
FIG. 8 is a schematic diagram of tissue perfusion and blood flow measured by an optical physiology measurement device according to an alternative embodiment of the present disclosure.

Referring to FIG. 5 again, the optical physiology measurement device 1' of the present disclosure is configured to measure physiological characteristics of a user via a skin surface S' of the user, wherein the physiological characteristics include tissue perfusion, blood flow, heart rate, respiration rate, blood oxygenation and so on. One method of measuring tissue perfusion according to the detected optical signals is to calculate a speckle contrast spatially, temporally or spatio-temporally according to acquired image frames, and calculate the tissue perfusion according to the calculated speckle contrast. One method of measuring tissue perfusion may be referred to "Review of laser speckle contrast techniques for visualizing tissue perfusion" by Matthijs Draijer et al. (2008). For example, FIG. 8 shows a schematic diagram of the measured tissue perfusion Sp and blood flow $S_{b1}$, wherein in one embodiment the blood flow $S_{b1}$ is an average intensity of the tissue perfusion Sp, but not limited thereto. A time interval $t_{pp}$ between two adjacent peaks of the tissue perfusion Sp may be used to calculate a heart rate. The heart rate is also obtainable by firstly converting the tissue perfusion Sp in time domain to a frequency domain and then calculating the heart rate according to the converted data in the frequency domain.

The optical physiology measurement device 1' includes a coherent light source 11', an image sensor 13', a processor 15' and a first communication interface 17'. As mentioned above, the optical physiology measurement device 1' is preferably encapsulated as a wireless single chip having a plurality of pins configured as the I/O interface. The processor 15' uses software, hardware, firmware or a combination thereof to calculate tissue perfusion Sp and/or blood flow $S_{b1}$ according to the method mentioned above, and the calculated tissue perfusion Sp and/or blood flow $S_{b1}$ are outputted using a wireless manner.

In some embodiments, the optical physiology measurement device 1' further includes an opaque sheet 12' positioned between the image sensor 13' and the skin surface S', wherein the opaque sheet 12' is configured to adjust an aperture of the image sensor 13' for better formation of speckle images by receiving scattered light. In some embodiments, the aperture of the opaque sheet 12' has a predetermined and fixed size. The shape and structure of the opaque sheet 12' do not have particular limitations as long as the image sensor 13' receives scattered light from tissues via an aperture of the opaque sheet 12'.

In some embodiments, the optical physiology measurement device 1' further includes at least one polarizer 14' and/or at least one filter 16' in front of a light receiving surface of the image sensor 13'. The polarizer 14' is configured to polarize the depolarized light scattered from the tissues. The filter 16' is configured to block light not emitted from the coherent light source 11' to allow the image sensor 13' to receive light only emitted by the coherent light source 11'. Preferably, the opaque sheet 12', the polarizer 14' and the filter 16' are also integrated in the wireless single chip. In other embodiments, the polarizer 14' and/or the filter 16' are formed on the wearable device 600 in which the optical physiology measurement device 1' integrated.

The coherent light source 11' is, for example, a laser diode for emitting infrared light or invisible light, and formed on a same substrate with the image sensor 13'. The light emitted by the coherent light source 11' preferably has a wavelength suitable for detecting human physiology, e.g., from 300 nm to 1100 nm. The coherent light source 11' is configured to illuminate the skin surface S' in a first brightness value and a second brightness value different from the first brightness value, e.g., referring to FIG. 3B. Preferably, an emitting surface of the coherent light source 11' is tightly and stably attached to the skin surface S' during the measurement so as to provide stable light.

The image sensor 13' is a CCD image sensor, a CMOS image sensor or the like having a plurality of pixels arranged in matrix. According to different applications, the image sensor 13' is a single photodiode to reduce the size and cost of the optical physiology measurement device 1'. The image sensor 13' is configured to receive scattered light, via the aperture of the opaque sheet 12', from tissues under the skin surface S', output a first image frame corresponding to the first brightness value and output a second image frame corresponding to the second brightness value. For example referring to FIG. 3B, the first image frame is shown to be $I_1$ and the second image frame is shown to be $I_2$, but not limited thereto. Similarly, during measurement, a detection surface of the image sensor 13' is preferably tightly and stably attached to the skin surface S' so as to stably receive light.

In the present disclosure, the optical physiology measurement device 1' identifies whether the coherent light source 11' and/or the image sensor 13' (e.g., a detection surface of the wireless single chip) are tightly or stably attached to the skin surface S' or not. If it is identified that the coherent light source 11' and/or the image sensor 13' are not tightly or stably attached to the skin surface S', the measurement process is stopped or the measured data is not shown on the display device 91' (described below).

The processor 15' is a digital signal processor and preferably formed on a same basis as the image sensor 13'. The processor 15' is electrically coupled to the coherent light source 11' and the image sensor 13'. The processor 15' has the ability to perform the calculation of the image data acquired by the image sensor 13' to obtain the tissue perfusion Sp and/or blood flow $S_{b1}$ using a predetermined algorithm, as shown in FIG. 8 for example.

The processor 15' of this embodiment is configured to calculate an intensity comparison index between the first image frame (e.g., $I_1$) and the second image frame (e.g., $I_2$), identify a contact status of the image sensor 13' (or the wireless single chip) with respect to the skin surface S' according to a comparison result of comparing the intensity comparison index with a threshold, and calculate tissue perfusion and/or blood flow according to at least one of the first image frame (e.g., $I_1$) and the second image frame (e.g., $I_2$). In this embodiment, the intensity comparison index is the average intensity difference (e.g., $B_1-B_2$) mentioned above or a ratio (e.g., $B_1/B_2$ or $B_2/B_1$) of an average intensity (e.g., $B_1$) of the first image frame $I_1$ with respect to an average intensity (e.g., $B_2$) of the second image frame $I_2$, but not limited thereto. The threshold is a predetermined threshold previously stored in the optical physiology measurement device 1' or is real-timely updated according to image frames captured by the image sensor 13'.

In this embodiment, if it is assumed that the first brightness value is larger than the second brightness value, the second image frame $I_2$ may or may not be used to calculate the tissue perfusion. That is, the second image frame $I_2$ is only used to identify the contact status of the optical physiology measurement device 1' with respect to the skin surface S' or is also used to calculate the tissue perfusion and/or blood flow.

More specifically, in one embodiment, the processor 15' is configured to calculate the tissue perfusion Sp and/or blood flow $S_{b1}$ (e.g., shown in FIG. 8) according to the first image frame $I_1$ but not according to the second image frame $I_2$. The second image frame $I_2$ is not used for its weaker intensity, e.g., the second brightness value being zero in some embodiments. In another embodiment, the processor 15' is configured to calculate the tissue perfusion Sp and/or blood flow $S_{b1}$ according to a differential image of the first image frame and the second image frame $I_2$. As mentioned above, by subtracting the second image frame $I_2$ from the first image frame $I_1$ in a pixel-by-pixel manner, the noise (e.g., thermal noise or pixel failure) is removed from the differential image.

The first communication interface 17' is a Bluetooth, Wi-Fi or the like capable of outputting the tissue perfusion Sp and/or blood flow $S_{b1}$ to an external electronic device in a wireless manner.

Figure 7:
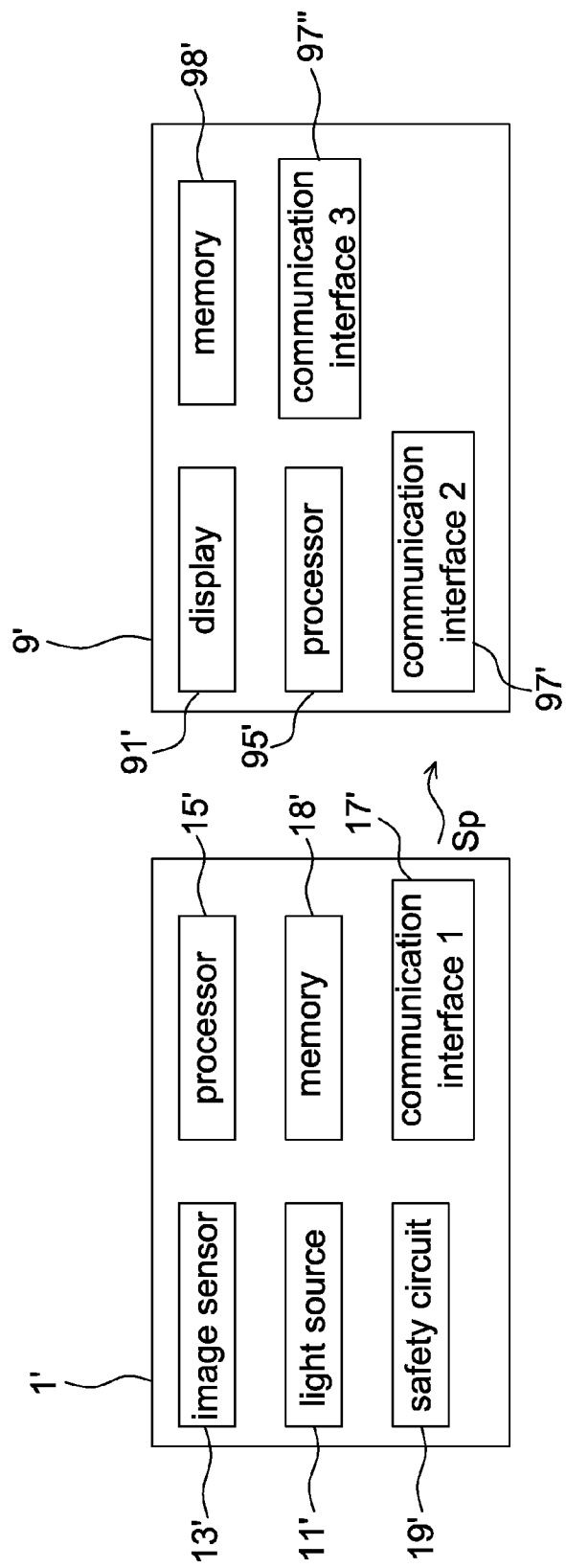
FIG. 7 is a block diagram of an optical physiology measurement system according to an alternative embodiment of the present disclosure.

Referring to FIG. 7, it is a schematic diagram of an optical physiology measurement system according to one embodiment of the present disclosure. The optical physiology measurement system includes the optical physiology measurement device 1' and an electronic device 9' wirelessly coupled together.

In FIG. 7, the optical physiology measurement device 1' is shown to further include a memory 18' and a safety circuit 19'. The memory 18' is a volatile memory, a nonvolatile memory or the both configured to store the algorithm for calculating the tissue perfusion and/or blood flow according to the captured image frames, and temporarily store the captured image data and operation parameters. The safety circuit 19' is configured to shut down the coherent light source 11' in unusual conditions, e.g., intensity of the captured image frame being unusually high, short circuit of the system, but not limited thereto.

The electronic device 9' includes a display device 91', a processor 95', a second communication interface 97' and a memory 98'. The processor 95' is electrically coupled to the display device 91', the second communication interface 97' and the memory 98'.

The second communication interface 97' is wirelessly coupled with the first communication interface 17' of the optical physiology measurement device 1' and configured to receive the tissue perfusion Sp and/or blood flow $S_{b1}$ from the optical physiology measurement device 1'. The method of the wireless coupling between two communication interfaces are known to the art and thus details thereof are not described herein.

The processor 95' is a microcontroller (MCU), a digital signal processor (DSP), an application specific integrated circuit (ASIC) or the like capable of post-processing the received tissue perfusion Sp and/or blood flow $S_{b1}$, e.g., filtering, interpolation, amplification, scaling and so on. The display device 91' has a screen and configured to show the tissue perfusion Sp and/or blood flow $S_{b1}$ on a screen thereof, e.g., referring to FIGS. 6A-6B.

It should be mentioned that although FIGS. 6A-6B shown that the display device 91' shows a variation curve of the tissue perfusion Sp in time, it is only intended to illustrate but not to limit the present disclosure. According to different applications, the display device 91' shows numerals rather than curves on the screen thereof, or shows both the tissue perfusion Sp and/or blood flow $S_{b1}$ by numerals and curves on the screen thereof.

The memory 98' is a volatile memory, a nonvolatile memory or the both. The memory 98' is configured as a buffer for the display device 9' to show the tissue perfusion Sp and/or blood flow $S_{b1}$, or for storing other algorithms and operation parameters used by the electronic device 9'. Said algorithms and operation parameters are different according to a type of the electronic device 9'.

In some embodiment, the electronic device 9' further includes a third communication interface 97", e.g., a wired or wireless interface, configured to communicate with other devices or equipment via internet, Wi-Fi or wireless phone system. More specifically, the third communication interface 97" is not coupled with the first communication interface 17' of the optical physiology measurement device 1'.

As mentioned above, the optical physiology measurement device 1' of the present disclosure is able to identify whether a detection surface of the wireless single chip is tightly or stably attached to the skin surface S'. For example, the processor 15' of the optical physiology measurement device 1' is further configured to control the first communication interface 17' not to output the tissue perfusion Sp and/or blood flow $S_{b1}$ when the intensity comparison index is smaller than the threshold. That is, when the intensity comparison index is smaller than the threshold, it means that the wireless single chip is not tightly or stably attached to the skin surface S'. In other embodiment, according to different processing of the image frames captured by the image sensor 13', the wireless single chip is identified not being tightly or stably attached to the skin surface S' when the intensity comparison index is larger than the threshold.

In other embodiment, when the optical physiology measurement device 1' identifies that a contact status is not suitable to calculate the tissue perfusion and/or blood flow (e.g., the intensity comparison index smaller than the threshold), the first communication interface 17' of the optical physiology measurement device 1' still outputs the calculated perfusion and/or blood flow data, but the display device 91' of the electronic device 9' is controlled not to show the perfusion and/or blood flow data received by the second communication interface 97' of the electronic device 9'.

As mentioned in FIGS. 3D and 3E, the optical physiology measurement device 1' of this embodiment is able to confirm a contact status between the image sensor 13' (or the wireless single chip) and a skin surface S'.

In one embodiment, the processor 15' of the optical physiology measurement device 1' is further configured to control the coherent light source 11' to monotonically change (increasing or decreasing) the first brightness value (e.g., shown in FIG. 3D), and identify whether the intensity comparison index is changed corresponding to the changing of the first brightness value. Details of this embodiment have been described above corresponding to FIG. 3D, and thus are not described herein.

In one embodiment, the processor 15' of the optical physiology measurement device 1' is further configured to monotonically change (increasing or decreasing) an exposure parameter of the image sensor 13' (e.g., shown in FIG. 3E), and identify whether the intensity comparison index is changed corresponding to the changing of the exposure parameter. Details of this embodiment have been described above corresponding to FIG. 3E, and thus are not described herein.

Figure 9:
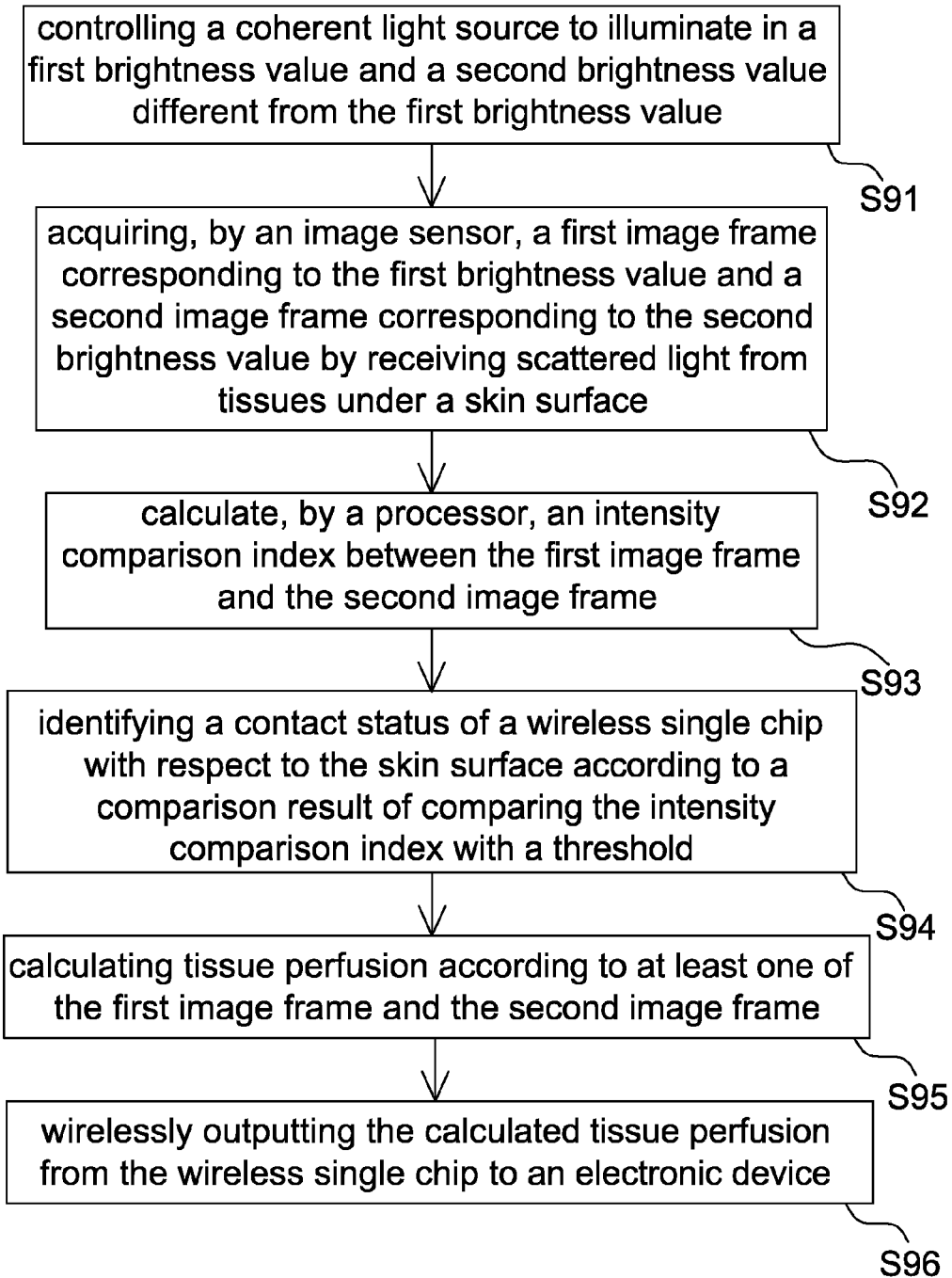
FIG. 9 is a flow chart of an operating method of a wireless single chip according to an alternative embodiment of the present disclosure.

Referring to FIG. 9, it is a flow chart of an operating method of a wireless single chip according to one embodiment of the present disclosure, wherein the operating method is, for example, applicable to the optical physiology measurement device 1' shown in FIG. 5. In this embodiment, the wireless single chip is preferably formed by encapsulating elements in the optical physiology measurement device 1' of FIGS. 5 and 7 in a wireless single chip. The wireless single chip includes a coherent light source 11', an image sensor 13', a processor 15' and a first communication interface 17', e.g., as shown in FIG. 7.

The operating method of this embodiment is configured to measure physiological characteristics of a user via a skin surface S' of the user, and includes the steps of: controlling a coherent light source to illuminate in a first brightness value and a second brightness value different from the first brightness value (Step S91); acquiring, by an image sensor, a first image frame corresponding to the first brightness value and a second image frame corresponding to the second brightness value by receiving scattered light from tissues under a skin surface (Step S92); calculate, by a processor, an intensity comparison index between the first image frame and the second image frame (Step S93); identifying, by the processor, a contact status of a wireless single chip with respect to the skin surface according to a comparison result of comparing the intensity comparison index with a threshold (Step S94); calculating, by the processor, tissue perfusion according to at least one of the first image frame and the second image frame (Step S95); and wirelessly outputting the calculated tissue perfusion from the wireless single chip to an electronic device (Step S96). In this embodiment, when the tissue perfusion is obtained, the blood flow is also obtainable according to the tissue perfusion.

Step S91: After the wearable device 600 (e.g., shown in FIGS. 6A and 6B) integrating the wireless single chip is carried by a user, the operation of the wireless single chip is started, e.g., the user pressing a button, receiving a start signal from an external electronic device 9', or having a contact sensor, but not limited thereto. The coherent light source 11' of the wireless single chip is controlled to illuminate light in a first brightness value and a second brightness value alternatively, e.g., as shown in FIG. 3B, wherein the second brightness value is larger or smaller than the first brightness value. The light from the coherent light source 11' is used to illuminate a skin surface S' of the user, and then the light penetrating into tissues propagates a distance in the tissues and then is scattered out from the skin surface S' again, as shown in FIG. 5. It is appreciated that a distance that the light propagating in the tissues and a distance between the elements shown in FIG. 5 are only intended to illustrate but not to limit the present disclosure.

Step S92: The image sensor 13' of the wireless single chip captures, via the aperture of the opaque sheet 12', the scattered light from the tissues in a frame rate, e.g., as shown in FIG. 3A. Due to the lighting of the coherent light source 11', the image sensor 13' acquires a first image frame $I_1$ corresponding to the first brightness value and a second image frame $I_2$ corresponding to the second brightness value, e.g., as shown in FIG. 3B.

Step S93: The processor 15' of the wireless single chip receives the first image frame $I_1$ and the second image frame $I_2$ from the image sensor 13', and calculates an intensity comparison index between the first image frame $I_1$ and the second image frame $I_2$. As mentioned above, the intensity comparison index is an average intensity difference or a ratio of an average intensity of the first image frame $I_1$ with respect to that of the second image frame $I_2$.

Step S94: In the present disclosure, the wireless single chip is able to identify a contact status thereof with respect to the skin surface S' being attached. For example, the processor 15' of the wireless single chip compares the intensity comparison index with a predetermined threshold, which is for example stored in the memory 18' previously or real-timely updated according to the image frames captured by the image sensor 13'. When the intensity comparison index is larger or smaller than (according to different applications) the predetermined threshold, the wireless single chip is identified not being tightly or stably attached to the skin surface S', and the processor 15' performs the predetermined control such as reducing the lighting frequency of the coherent light source 11', reducing the frame rate of the image sensor 13', not calculating the tissue perfusion and/or blood flow data, controlling the first communication interface 17' not to output the calculated tissue perfusion and/or blood flow data, and/or controlling the display device (e.g., 91' shown in FIGS. 6A and 6B) not to show the received tissue perfusion and/or blood flow data, but not limited thereto. When the wireless single chip is identified to be stably attached to the skin surface S', the wireless single chip operates normally, e.g., calculating and outputting the calculated tissue perfusion and/or blood flow data.

Step S95: The processor 15' of the wireless single chip calculates tissue perfusion Sp and/or blood flow $S_{b1}$, e.g., as shown in FIG. 8, according to the first image frame $I_1$ and/or the second image frame $I_2$. As mentioned above, if the second brightness value is selected to be smaller than the first brightness value, the second image frame $I_2$ may or may not be used to calculate the tissue perfusion and/or blood flow according to different applications.

Step S96: Finally, the first communication interface 17' of the wireless single chip is configured to send (e.g., in a report rate) the calculated tissue perfusion and/or blood flow to an external electronic device 9' for being shown on a screen thereof. In the present disclosure, the wireless single chip is not used to output image raw data captured by the image sensor 13' to the external electronic device 9'. More specifically, the electronic device 9' does not calculate the tissue perfusion according to the image frames captured by the image sensor 13'.

It should be mentioned that although FIG. 9 shows that the Step S93 is prior to the Step S95, it is not to limit the present disclosure. In other embodiments, the Step S95 is performed simultaneously or prior to the Step S93 according to different applications.

In addition, the wireless single chip is able to further confirm the contact status between the wireless single chip and the skin surface S' by changing the illuminating intensity and the exposure time.

In one application, the operating method of this embodiment further includes a step of: monotonically changing the first brightness value of the coherent light source 11', and identifying whether the intensity comparison index is changed corresponding to the first brightness value (as shown in FIG. 3D).

In one application, the operating method of this embodiment further includes a step of: monotonically changing an exposure parameter of the image sensor 13', and identifying whether the intensity comparison index is changed corresponding to the exposure parameter (as shown in FIG. 3E).

It should be mentioned that although the above embodiments take a reflective physiology measurement device, i.e. the coherent light source 11' and the image sensor 13' at a same side of tissues of interest, as an example, it is only intended to illustrate but not to limit the present disclosure. In other embodiments, the optical physiology measurement device 1' of the present disclosure is a transmissive physiology measurement device, i.e. the coherent light source 11' and the image sensor 13' at opposite sides of tissues of interest.

It should be mentioned that although FIGS. 5 and 7 show that the optical physiology measurement device 1' includes one coherent light source 11', they are only intended to illustrate but not to limit the present disclosure. According to different applications, the optical physiology measurement device 1' includes another light source, e.g., a coherent or non-coherent light source of different emitting wavelength such that it is possible to measure the blood oxygenation. In addition, the method of testing whether the wireless single chip is tightly or stably attached to the skin surface S' using two light sources, e.g., FIG. 3C, is implemented by this arrangement. More specifically, the method showing in FIGS. 3A-3E are applicable to the physiology measurement by changing the work surface shown in FIG. 1 to the skin surface S' shown in FIG. 5, and changing the lift state in the previous embodiment to the contact state of the alternative embodiment. In the alternative embodiment, the processor 15' calculates the physiology characteristics but does not calculate the displacement.

As mentioned above, a contact status between a detection surface of an optical physiology measurement means and a skin surface of interest can significantly affect detection results. Accordingly, the present disclosure further provides an optical physiology measurement device (FIG. 5), an optical physiology measurement system (FIG. 7) and an operating method of a wireless single chip (FIG. 9) that display correct measured data only when the optical physiology measurement means is stably and tightly attached to the skin surface.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. An optical physiology measurement device, configured to measure physiological characteristics of a user via a skin surface of the user, the optical physiology measurement device comprising:

a coherent light source configured to illuminate the skin surface in a first brightness value and a second brightness value different from the first brightness value;
an image sensor configured to receive scattered light from tissues under the skin surface, output a first image frame corresponding to the first brightness value and output a second image frame corresponding to the second brightness value; and
a processor electrically coupled to the light source and the image sensor, and configured to
calculate an intensity comparison index between the first image frame and the second image frame,
identify a contact status of the image sensor with respect to the skin surface according to a comparison result of comparing the intensity comparison index with a threshold, and
calculate tissue perfusion according to at least one of the first image frame and the second image frame.

2. The optical physiology measurement device as claimed in claim 1, wherein the first brightness value is larger than the second brightness value, and the processor is configured to calculate the tissue perfusion according to the first image frame but not according to the second image frame.

3. The optical physiology measurement device as claimed in claim 1, wherein the processor is configured to calculate the tissue perfusion according to a differential image of the first image frame and the second image frame.

4. The optical physiology measurement device as claimed in claim 1, wherein the optical physiology measurement device is a reflective physiology measurement device.

5. The optical physiology measurement device as claimed in claim 1, further comprising a wireless communication interface configured to output the tissue perfusion.

6. The optical physiology measurement device as claimed in claim 5, wherein the processor is further configured to control the wireless communication interface not to output the tissue perfusion when the intensity comparison index is smaller than the threshold.

7. The optical physiology measurement device as claimed in claim 1, wherein the processor is further configured to
control the coherent light source to monotonically change the first brightness value, and
identify whether the intensity comparison index is changed corresponding to the first brightness value.

8. The optical physiology measurement device as claimed in claim 1, wherein the processor is further configured to
monotonically change an exposure parameter of the image sensor, and
identify whether the intensity comparison index is changed corresponding to the exposure parameter.

9. A physiology measurement system, configured to measure physiological characteristics of a user via a skin surface of the user, the physiology measurement system comprising:
an optical physiology measurement device comprising:
a coherent light source configured to illuminate the skin surface in a first brightness value and a second brightness value different from the first brightness value;
an image sensor configured to receive scattered light from tissues under the skin surface, output a first image frame corresponding to the first brightness value and output a second image frame corresponding to the second brightness value;
a processor electrically coupled to the light source and the image sensor, and configured to calculate an intensity comparison index between the first image frame and the second image frame, identify a contact status of the image sensor with respect to the skin surface according to the intensity comparison index, and calculate tissue perfusion according to at least one of the first image frame and the second image frame; and
a first communication interface configured to output the tissue perfusion; and
an electronic device wirelessly coupled to the optical physiology measurement device and comprising:
a second communication interface configured to receive the tissue perfusion from the optical physiology measurement device; and
a display device configured to show the tissue perfusion on a screen thereof.

10. The physiology measurement system as claimed in claim 9, wherein
the optical physiology measurement device is integrated in a wearable device, and
the electronic device is a portable electronic device.

11. The physiology measurement system as claimed in claim 9, wherein the first brightness value is larger than the second brightness value, and the processor is configured to calculate the tissue perfusion according to the first image frame but not according to the second image frame.

12. The physiology measurement system as claimed in claim 9, wherein the processor is configured to calculate the tissue perfusion according to a differential image of the first image frame and the second image frame.

13. The physiology measurement system as claimed in claim 9, wherein the processor is configured to identify the contact status of the image sensor with respect to the skin surface according to a comparison result of comparing the intensity comparison index with a threshold.

14. The physiology measurement system as claimed in claim 13, wherein the processor is further configured to control the first communication interface not to output the tissue perfusion when the intensity comparison index is smaller than the threshold.

15. The physiology measurement system as claimed in claim 9, wherein the optical physiology measurement device is a wireless single chip.

16. An operating method of a wireless single chip, configured to measure physiological characteristics of a user via a skin surface of the user, the wireless single chip comprising a coherent light source, an image sensor and a processor, the operating method comprising:
controlling the coherent light source to illuminate the skin surface in a first brightness value and a second brightness value different from the first brightness value;
acquiring, by the image sensor, a first image frame corresponding to the first brightness value and a second image frame corresponding to the second brightness value by receiving scattered light from tissues under the skin surface;
calculate, by the processor, an intensity comparison index between the first image frame and the second image frame;
identifying, by the processor, a contact status of the wireless single chip with respect to the skin surface according to a comparison result of comparing the intensity comparison index with a threshold; and
calculating, by the processor, tissue perfusion according to at least one of the first image frame and the second image frame.

17. The operating method as claimed in claim 16, wherein the calculating comprising:

calculating a speckle contrast spatially, temporally or spatio-temporally according to at least one of the first image frame and the second image frame; and calculating the tissue perfusion according to the calculated speckle contrast.

18. The operating method as claimed in claim 16, further comprising:

monotonically changing the first brightness value of the coherent light source, and identifying whether the intensity comparison index is changed corresponding to the first brightness value.

19. The operating method as claimed in claim 16, further comprising:

monotonically changing an exposure parameter of the image sensor, and identifying whether the intensity comparison index is changed corresponding to the exposure parameter.

20. The operating method as claimed in claim 16, wherein the wireless single chip further comprises a communication interface and the operating method further comprises:

wirelessly outputting the calculated tissue perfusion from the wireless single chip to an electronic device.

* * * * *